US012702266B2

(12) United States Patent
Michihata

(10) Patent No.: US 12,702,266 B2
(45) Date of Patent: Aug. 11, 2026

(54) MEDICAL CONTROL DEVICE AND MEDICAL OBSERVATION SYSTEM USING A DIFFERENT WAVELENGTH BAND THAN THAT OF FLUORESCENCE OF AN OBSERVATION TARGET TO CONTROL FOCUS OR BRIGHTNESS

(71) Applicant: Sony Olympus Medical Solutions Inc., Tokyo (JP)

(72) Inventor: Taihei Michihata, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 1078 days.

(21) Appl. No.: 17/129,943

(22) Filed: Dec. 22, 2020

(65) Prior Publication Data

US 2021/0290035 A1 Sep. 23, 2021

(30) Foreign Application Priority Data

Mar. 18, 2020 (JP) ................................ 2020-047499

(51) Int. Cl.
*A61B 5/00* (2006.01)
*A61B 1/00* (2006.01)
(Continued)

(52) U.S. Cl.
CPC ...... *A61B 1/00006* (2013.01); *A61B 1/00009* (2013.01); *A61B 1/000095* (2022.02);
(Continued)

(58) Field of Classification Search
CPC .......... A61B 1/000095; A61B 1/00002; A61B 1/00188; A61B 1/06; A61B 1/0638
See application file for complete search history.

(56) References Cited

U.S. PATENT DOCUMENTS 11,432,712 B2 * 9/2022 Duckett, III ........... H04N 23/11
2003/0135092 A1 * 7/2003 Cline .................. A61B 1/0655
600/178
(Continued)

FOREIGN PATENT DOCUMENTS

JP H10201707 A 8/1998
JP 2013061618 A 4/2013
(Continued)

OTHER PUBLICATIONS

English Translation of JP-2013182219.*
English Translation of WO 2015012096.*

*Primary Examiner* — Tse W Chen
*Assistant Examiner* — Martin Nathan Ortega
(74) *Attorney, Agent, or Firm* — XSENSUS LLP

(57) ABSTRACT

A medical control device includes: a light source controller configured to control a light source configured to emit excitation light in a first wavelength band and light in a second wavelength band; a captured image acquiring unit configured to acquire a captured image obtained by capturing an image of an observation target irradiated with light emitted from the light source; an evaluation value calculator configured to calculate, based on the captured image, an evaluation value used for at least one of a first control for controlling a focal position of an imaging device configured to generate the captured image or a second control for controlling a brightness of the captured image; an operation controller configured to perform, based on the evaluation value, at least one of the first control or the second control; and an adjustment processing execution unit configured to perform adjustment processing on the captured image.

20 Claims, 9 Drawing Sheets

(51) Int. Cl.

| | |
|---|---|
| ***A61B 1/04*** | (2006.01) |
| ***A61B 1/06*** | (2006.01) |
| ***A61K 49/00*** | (2006.01) |

(52) U.S. Cl.

CPC .......... *A61B 1/00188* (2013.01); *A61B 1/043* (2013.01); *A61B 1/0638* (2013.01); *A61B 1/0655* (2022.02); *A61B 1/0661* (2013.01); *A61K 49/0036* (2013.01)

(56) References Cited

U.S. PATENT DOCUMENTS

| | | | | |
|---|---|---|---|---|
| 2005/0143627 | A1* | 6/2005 | Cline | A61B 1/0638 600/109 |
| 2006/0058684 | A1* | 3/2006 | Sendai | A61B 1/00186 600/476 |
| 2008/0249368 | A1* | 10/2008 | Takei | A61B 1/0655 600/181 |
| 2014/0267626 | A1* | 9/2014 | Lilagan | A61B 1/00193 348/46 |
| 2016/0227992 | A1* | 8/2016 | Yoshino | A61B 1/00188 |
| 2018/0000401 | A1* | 1/2018 | Kang | A61B 1/063 |
| 2018/0316870 | A1* | 11/2018 | Yoshino | H04N 23/6811 |
| 2019/0087970 | A1* | 3/2019 | Endo | A61B 1/000094 |
| 2019/0379840 | A1* | 12/2019 | Frangioni | A61B 1/0005 |
| 2021/0006757 | A1* | 1/2021 | Aoyama | H04N 25/135 |

FOREIGN PATENT DOCUMENTS

| | | | | |
|---|---|---|---|---|
| JP | 2013182219 A * | 9/2013 | | |
| WO | WO-2015012096 A1 * | 1/2015 | | A61B 1/00006 |
| WO | WO-2018178269 A1 * | 10/2018 | | A61B 3/1025 |
| WO | WO-2021019597 A1 * | 2/2021 | | |

* cited by examiner

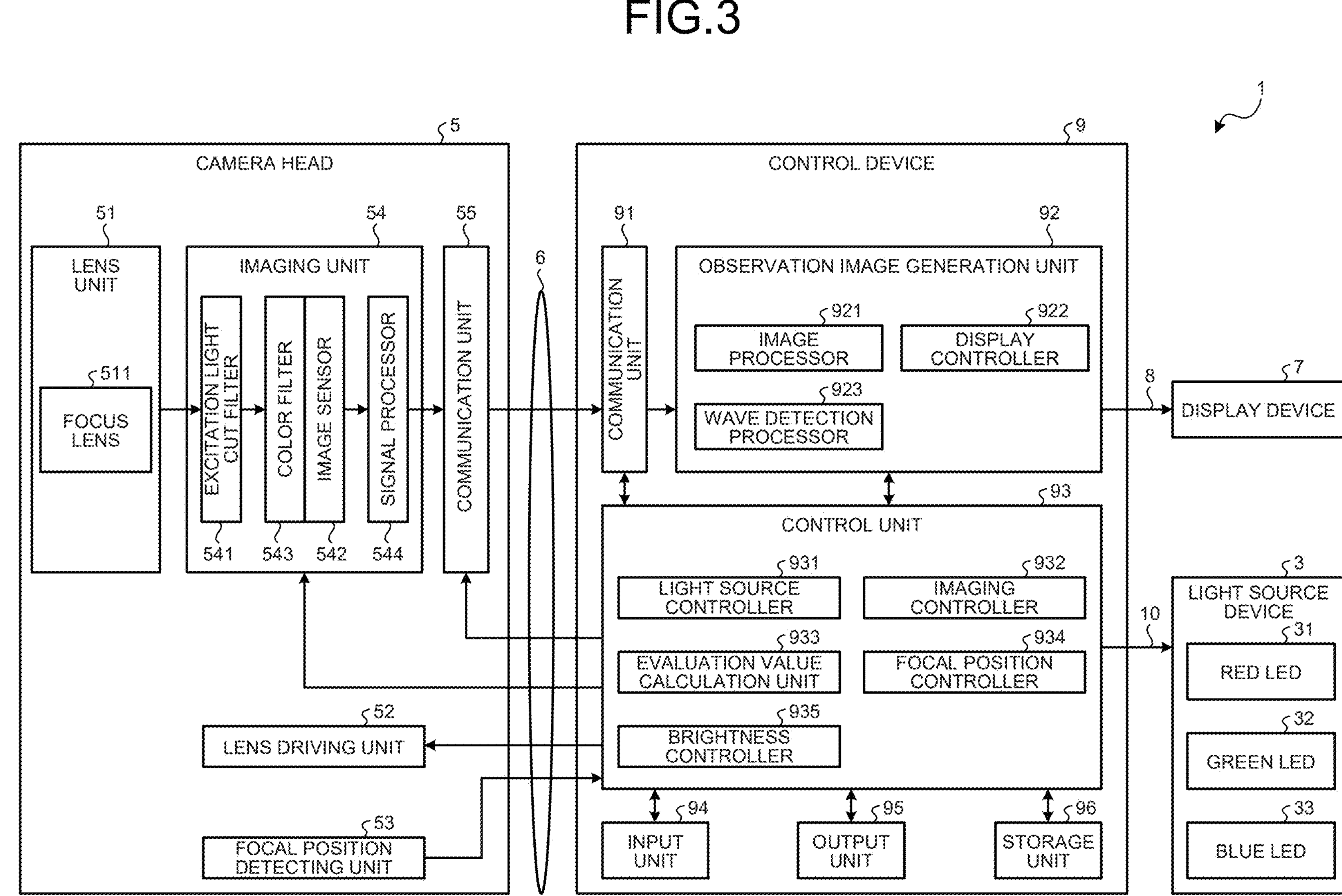
FIG.3
1
CAMERA HEAD
5
LENS UNIT
51
FOCUS LENS
511
IMAGING UNIT
54
EXCITATION LIGHT CUT FILTER
541
COLOR FILTER
543
IMAGE SENSOR
542
SIGNAL PROCESSOR
544
COMMUNICATION UNIT
55
LENS DRIVING UNIT
52
FOCAL POSITION DETECTING UNIT
53
6
CONTROL DEVICE
9
COMMUNICATION UNIT
91
OBSERVATION IMAGE GENERATION UNIT
92
IMAGE PROCESSOR
921
DISPLAY CONTROLLER
922
WAVE DETECTION PROCESSOR
923
CONTROL UNIT
93
LIGHT SOURCE CONTROLLER
931
IMAGING CONTROLLER
932
EVALUATION VALUE CALCULATION UNIT
933
FOCAL POSITION CONTROLLER
934
BRIGHTNESS CONTROLLER
935
INPUT UNIT
94
OUTPUT UNIT
95
STORAGE UNIT
96
8
DISPLAY DEVICE
7
10
LIGHT SOURCE DEVICE
3
RED LED
31
GREEN LED
32
BLUE LED
33

FIG.10

MEDICAL CONTROL DEVICE AND MEDICAL OBSERVATION SYSTEM USING A DIFFERENT WAVELENGTH BAND THAN THAT OF FLUORESCENCE OF AN OBSERVATION TARGET TO CONTROL FOCUS OR BRIGHTNESS

CROSS-REFERENCE TO RELATED APPLICATION

This application claims priority from Japanese Application No. 2020-047499, filed on Mar. 18, 2020, the contents of which are incorporated by reference herein in its entirety.

BACKGROUND

The present disclosure relates to a medical control device and a medical observation system.

In the related art, a photodynamic diagnostic apparatus for performing photodynamic diagnosis (PDD), which is one of cancer diagnostic methods for detecting cancer cells, has been known (for example, see JP 2016-202726 A).

In photodynamic diagnosis, for example, a photosensitive substance such as 5-aminolevulinic acid (hereinafter, referred to as 5-ALA) is used. The 5-ALA is a natural amino acid originally contained in the living body of animals and plants. This 5-ALA is taken up into cells after administration into the body and biosynthesized into protoporphyrin in mitochondria. Then, in cancer cells, the protoporphyrin is excessively accumulated. In addition, the protoporphyrin that is excessively accumulated in the cancer cells is photoactive. Therefore, when the protoporphyrin is excited by excitation light (for example, blue visible light in a wavelength band of 375 nm to 445 nm), the protoporphyrin emits fluorescence (for example, red fluorescence in a wavelength band of 600 nm to 740 nm). A cancer diagnostic method in which a photosensitive substance is used to make cancer cells fluoresce in this way is called photodynamic diagnosis.

The photodynamic diagnostic apparatus described in JP 2016-202726 A includes a fluorescence imaging device that captures an image of fluorescence from a photosensitive substance excited by excitation light to generate a fluorescence image, and an optical filter that is provided on an upstream side of an optical path of the fluorescence imaging device and cuts entire excitation light directed to the fluorescence imaging device.

SUMMARY

In the fluorescence image, a signal level is remarkably low because the fluorescence from the photosensitive substance is minute.

Therefore, it is not possible to calculate an appropriate evaluation value even in a case of calculating, based on the fluorescence image, an evaluation value used for a first control for controlling a focal position of an imaging unit or a second control for controlling the brightness of the fluorescence image.

Here, it is conceivable to contain, in the fluorescence image, an excitation light component by transmitting a part of the excitation light, rather than cutting the entire excitation light directed to the fluorescence imaging device by using the optical filter. However, the excitation light is not light in a green wavelength band that contributes to the brightness that is easy for humans to see, but is light in a blue wavelength band that hardly contributes to the brightness. Therefore, even in a case of calculating the above-described evaluation value based on the fluorescence image containing the excitation light component, an appropriate evaluation value still may not be calculated.

As a result, the evaluation value is not appropriate, the first control or the second control may not be properly performed, and an image suitable for observation may not be generated, which is problematic.

There is a need for a medical control device and a medical observation system that are able to generate an image suitable for observation.

According to one aspect of the present disclosure, there is provided a medical control device including: a light source controller configured to control an operation of a light source configured to emit excitation light in a first wavelength band and light in a second wavelength band different from the first wavelength band; a captured image acquiring unit configured to acquire a captured image obtained by capturing an image of an observation target irradiated with light emitted from the light source; an evaluation value calculator configured to calculate, based on the captured image, an evaluation value used for at least one of a first control for controlling a focal position of an imaging device configured to generate the captured image or a second control for controlling a brightness of the captured image; an operation controller configured to perform, based on the evaluation value, at least one of the first control or the second control; and an adjustment processing execution unit configured to perform adjustment processing on the captured image, wherein the light source controller is configured to control the operation of the light source such that a component of the light in the second wavelength band is contained in the captured image used for the calculation of the evaluation value, and the adjustment processing execution unit is configured to perform the adjustment processing for removing the component of the light in the second wavelength band contained in the captured image.

BRIEF DESCRIPTION OF THE DRAWINGS

FIG. 3 is a block diagram illustrating a configuration of a camera head and a control device;

FIG. 10 is a diagram illustrating a configuration of a medical observation system according to a fourth embodiment.

DETAILED DESCRIPTION

Figure 1:
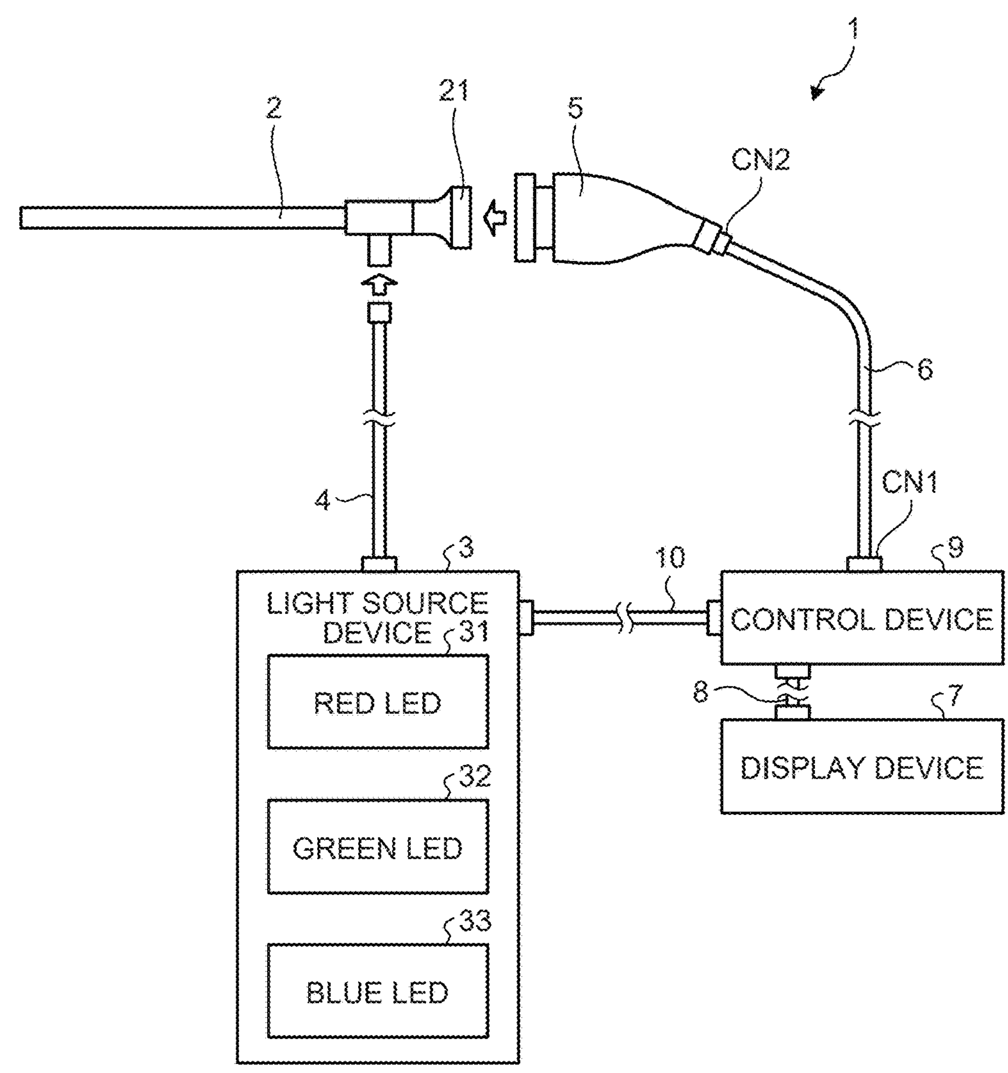
FIG. 1 is a diagram illustrating a configuration of a medical observation system according to a first embodiment.

Hereinafter, embodiments for carrying out the present disclosure (hereinafter, referred to as embodiments) will be described with reference to the drawings. Note that the present disclosure is not limited to the embodiments described below. Further, in the description of the drawings, the same reference numerals denote the same parts.

First Embodiment

Schematic Configuration of Medical Observation System

FIG. 1 is a diagram illustrating a configuration of a medical observation system 1 according to a first embodiment.

The medical observation system 1 is a system used in the medical field to capture (observe) an image of the inside of a living body (observation target) as a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 is implemented by a rigid endoscope. That is, the insertion unit 2 has an elongated shape and is entirely hard, or is partially hard and partially soft, and the insertion unit 2 is inserted into the living body. In the insertion unit 2, an optical system, which includes one or more lenses and collects light from the subject, is provided.

Figure 2:
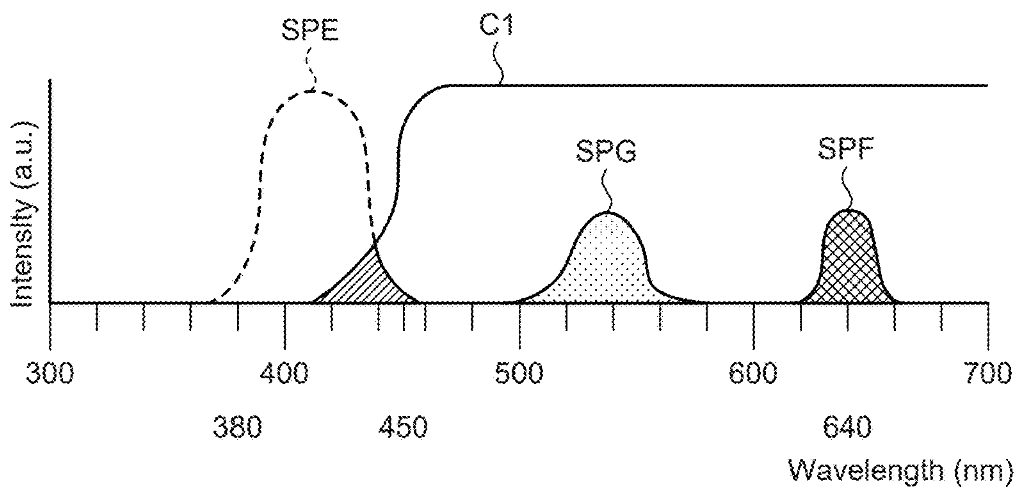
FIG. 2 is a diagram illustrating a spectrum of light emitted from a light source device.

FIG. 2 is a diagram illustrating a spectrum of light emitted from the light source device 3.

The light source device 3 supplies light for illuminating the inside of the living body to one end of the light guide 4 under the control of the control device 9. In the first embodiment, the light source device 3 includes a red light emitting diode (LED) 31, a green LED 32, and a blue LED 33, as illustrated in FIG. 1.

The red LED 31 is an LED that emits light in a red wavelength band.

The green LED 32 is an LED that emits light in a second wavelength band including a green wavelength band. The blue LED 33 is an LED that emits excitation light in a first wavelength band. In the first embodiment, the excitation light in the first wavelength band is excitation light in a blue wavelength band (for example, a wavelength band of 375 nm to 445 nm) that excites protoporphyrin, as shown by a spectrum SPE illustrated in FIG. 2. Further, the protoporphyrin emits fluorescence in the red wavelength band (for example, a wavelength band of 600 nm to 740 nm) when excited by the excitation light, as shown by a spectrum SPF illustrated in FIG. 2.

Here, in the first embodiment, the light in the second wavelength band that is emitted by the green LED 32 is, for example, light in a wavelength band of 500 nm to 560 nm, as shown by a spectrum SPG illustrated in FIG. 2. That is, the light in the second wavelength band is a narrow band light that does not include the wavelength band of the fluorescence described above. Note that, in the following description, the light in the second wavelength band will be referred to as G color light for convenience of explanation.

Then, in the light source device 3 according to the first embodiment, the green LED 32 and the blue LED 33 are simultaneously driven under the control of the control device 9. That is, the light source device 3 simultaneously emits the excitation light and the G color light.

Note that, in the first embodiment, the light source device 3 includes three LEDs 31 to 33 in order to be able to emit white light, but the present disclosure is not limited thereto, and may have a configuration in which the red LED 31 is not provided (a configuration in which only the green LED 32 and the blue LED 33 are included). Further, the green LED 32 and the blue LED 33 are not limited to LEDs, and may be implemented by semiconductor lasers or the like. Further, the light source device 3 is configured as a separate component from the control device 9, but the present disclosure is not limited thereto, and a configuration in which the light source device 3 is provided inside the control device 9 may be adopted.

The light guide 4 has one end detachably connected to the light source device 3, and the other end detachably connected to the insertion unit 2. Further, the light guide 4 transmits the light emitted from the light source device 3 from one end to the other end to supply the light to the insertion unit 2. The emitted light (excitation light and G color light) supplied to the insertion unit 2 is emitted from a distal end of the insertion unit 2 and is radiated into the living body. The excitation light radiated into the living body and reflected in the living body, the G color light reflected in the living body, and fluorescence that is emitted from protoporphyrin as the protoporphyrin accumulated in a lesion in the living body is excited are collected by the optical system in the insertion unit 2. Note that, in the following description, the excitation light, the G color light, and the fluorescence collected by the optical system in the insertion unit 2 are referred to as subject images for convenience of explanation.

The camera head 5 corresponds to an imaging device according to the present disclosure. The camera head 5 is detachably connected to a proximal end (eyepiece 21 (FIG. 1)) of the insertion unit 2. Further, the camera head 5 captures the subject images (excitation light, G color light, and fluorescence) collected by the insertion unit 2 under the control of the control device 9, and outputs an image signal (RAW signal) obtained by the image capturing. The image signal is, for example, an image signal of 4K or higher.

Note that a detailed configuration of the camera head 5 will be described later.

The first transmission cable 6 has one end detachably connected to the control device 9 via a connector CN1 (FIG. 1), and the other end detachably connected to the camera head 5 via a connector CN2 (FIG. 1). Further, the first transmission cable 6 transmits the image signal or the like output from the camera head 5 to the control device 9, and also transmits, to the camera head 5, each of a control signal, a synchronization signal, a clock, power, and the like output from the control device 9.

Note that, in the transmission of the image signal or the like from the camera head 5 to the control device 9 via the first transmission cable 6, the image signal or the like may be transmitted as an optical signal or as an electric signal. The same applies to the transmission of the control signal, the synchronization signal, and the clock from the control device 9 to the camera head 5 via the first transmission cable 6.

The display device 7 is implemented by a display using liquid crystal, organic electroluminescence (EL), or the like, and displays an image based on a video signal from the control device 9 under the control of the control device 9.

The second transmission cable 8 has one end detachably connected to the display device 7, and the other end detachably connected to the control device 9. Further, the second transmission cable 8 transmits the video signal processed by the control device 9 to the display device 7.

The control device 9 corresponds to a medical control device according to the present disclosure. The control device 9 is implemented by a central processing unit (CPU), a field-programmable gate array (FPGA), or the like, and integrally controls operations of the light source device 3, the camera head 5, and the display device 7.

Note that a detailed configuration of the control device 9 will be described later.

The third transmission cable 10 has one end detachably connected to the light source device 3, and the other end detachably connected to the control device 9. Further, the third transmission cable 10 transmits a control signal from the control device 9 to the light source device 3.

Configuration of Camera Head

Next, the configuration of the camera head 5 will be described.

FIG. 3 is a block diagram illustrating the configurations of the camera head 5 and the control device 9.

Note that the connectors CN1 and CN2 between the first transmission cable 6 and each of the control device 9 and the camera head 5, connectors between the second transmission cable 8 and each of the control device 9 and the display device 7, and connectors between the third transmission cable 10 and each of the control device 9 and the light source device 3 are not illustrated in FIG. 3 for convenience of explanation.

As illustrated in FIG. 3, the camera head 5 includes a lens unit 51, a lens driving unit 52, a focal position detecting unit 53, an imaging unit 54, and a communication unit 55.

The lens unit 51 includes a focus lens 511 and has a function of forming subject images (excitation light, G color light, and fluorescence) collected by the insertion unit 2 on an imaging surface of the imaging unit 54 (image sensor 542).

The focus lens 511 includes one or more lenses, and adjusts a focal position by moving along an optical axis. Further, a focus mechanism (not illustrated) for moving the focus lens 511 along the optical axis is provided in the lens unit 51.

The lens driving unit 52 operates the above-described focus mechanism under the control of the control device 9 in AF (Auto Focus) processing as described later, the AF processing being performed by the control device 9, and adjusts a focal position of the lens unit 51.

The focal position detecting unit 53 is implemented by a position sensor such as a photo interrupter, and detects a current position (focal position) of the focus lens 511. Further, the focal position detecting unit 53 outputs a signal corresponding to the detected focal position to the control device 9.

The imaging unit 54 captures an image of the inside of the living body under the control of the control device 9. As illustrated in FIG. 3, the imaging unit 54 includes an excitation light cut filter 541, the image sensor 542, a color filter 543, and a signal processor 544.

The excitation light cut filter 541 is provided between the lens unit 51 and the image sensor 542, and has a transmission characteristic of transmitting light in a wavelength band of about 410 nm or more therethrough as indicated by a curve C1 in FIG. 2. That is, the excitation light cut filter 541 transmits the entire G color light and fluorescence and transmits only a part of the excitation light, among the subject images (excitation light, G color light, and fluorescence) directed from the lens unit 51 to the image sensor 542.

The image sensor 542 is implemented by a charge coupled device (CCD), a complementary metal oxide semiconductor (CMOS), or the like that receives light with which an image is formed by the lens unit 51 and converts the light into an electric signal (analog signal). In the following description, for convenience of explanation, a captured image generated by capturing the subject images (excitation light, G color light, and fluorescence) with the image sensor 542 will be referred to as a PDD image.

Figure 4:
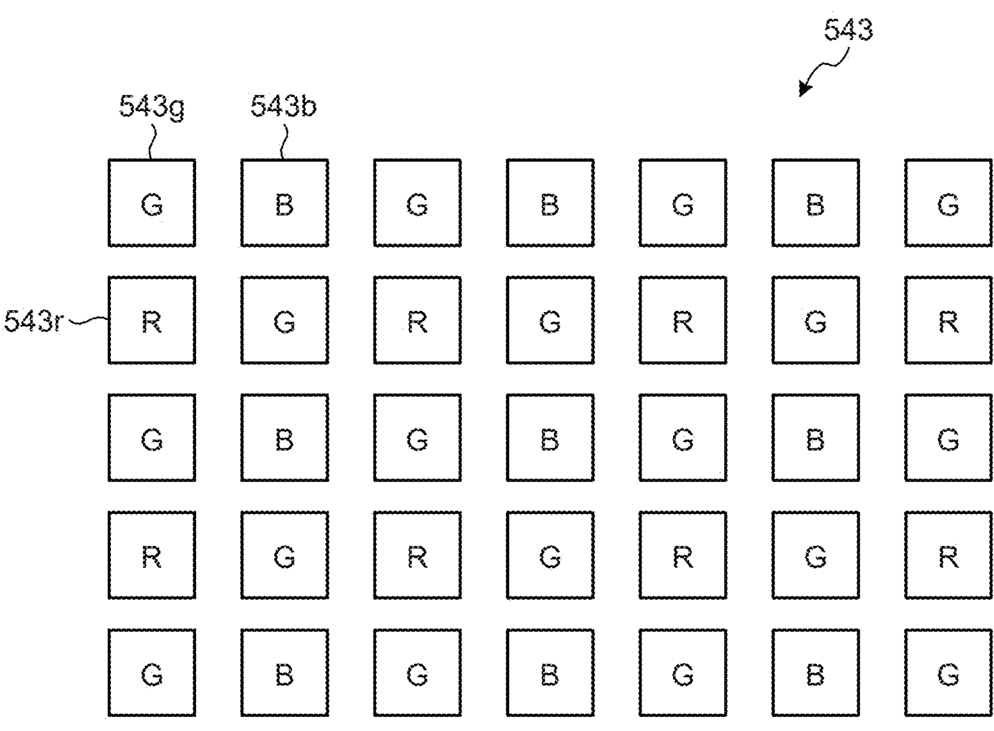
FIG. 4 is a diagram illustrating a color filter.

FIG. 4 is a diagram illustrating the color filter 543.

The color filter 543 is a color filter which is provided on an imaging surface (light receiving surface) of the image sensor 542, and in which three filter groups formed according to the wavelength bands of light (R (red), G (green), B (blue)) to be transmitted are arranged in a specific pattern (for example, a Bayer array).

Specifically, as illustrated in FIG. 4, the color filter 543 includes an R filter group 543*r* that mainly transmits light in the red wavelength band, a B filter group 543*b* that mainly transmits light in the blue wavelength band, a first G filter group (arranged in the same column as the R filter group 543*r*) that mainly transmits light in the green wavelength band, and a second G filter group (arranged in the same column as the B filter group 543*b*) that mainly transmits light in the green wavelength band. Note that, in FIG. 4, the first and second G filter groups are collectively referred to as a G filter group 543*g*. Further, in FIG. 4, the R filter group 543*r* is indicated by the letter "R", the G filter group 543*g* is indicated by the letter "G", and the B filter group 543*b* is indicated by the letter "B".

Under the control of the control device 9, the signal processor 544 performs signal processing on the PDD image (analog signal) generated by the image sensor 542 and outputs the PDD image (RAW signal (digital signal)).

For example, the signal processor 544 performs, on the PDD image (analog signal) generated by the image sensor 542, processing of removing reset noise, processing of multiplying an analog gain for amplifying the analog signal, and signal processing such as A/D conversion.

The communication unit 55 functions as a transmitter that transmits the PDD image (RAW signal (digital signal)) output from the imaging unit 54 to the control device 9 via the first transmission cable 6. The communication unit 55 is implemented by, for example, a high-speed serial interface that performs communication with the control device 9 for a PDD image at a transmission rate of 1 Gbps or more via the first transmission cable 6.

Configuration of Control Device

Next, the configuration of the control device 9 will be described with reference to FIG. 3.

As illustrated in FIG. 3, the control device 9 includes a communication unit 91, an observation image generation unit 92, a control unit 93, an input unit 94, an output unit 95, and a storage unit 96.

The communication unit 91 functions as a receiver that receives a PDD image (RAW signal (digital signal)) output from the camera head 5 (communication unit 55) via the first transmission cable 6. That is, the communication unit 91 corresponds to a captured image acquiring unit according to the present disclosure. The communication unit 91 is implemented by, for example, a high-speed serial interface that performs communication with the communication unit 55 for a PDD image at a transmission rate of 1 Gbps or more.

Under the control of the control unit 93, the observation image generation unit 92 processes PDD images (RAW signals (digital signals)) that are sequentially output from the camera head 5 (communication unit 55) and received by the communication unit 91. As illustrated in FIG. 3, the observation image generation unit 92 includes an image processor 921, a display controller 922, and a wave detection processor 923.

The image processor 921 performs first and second image processing on the input PDD image (RAW signal (digital signal)).

Examples of the first image processing may include optical black subtraction processing, white balance adjustment processing, digital gain processing, demosaic processing, color correction matrix processing, gamma correction processing, YC processing of converting an RGB signal (PDD image) into a luminance signal and a chrominance signal (Y, CB/CR signal).

In addition, the second image processing includes adjustment processing as below.

The adjustment processing is processing of removing a component of the G color light contained in the PDD image. Specifically, the excitation light is light in the blue wavelength band (for example, the wavelength band of 375 nm to 445 nm). Further, the G color light is light in the green wavelength band (for example, the wavelength band of 500 nm to 560 nm). In addition, the fluorescence is light in the red wavelength band (for example, the wavelength band of 600 nm to 740 nm). Further, in the adjustment processing, among R, G, and B pixel values included in the PDD image, the G value is removed (the G value is set to "0"), and the B value and the R value are remained, the G value being a component of the G color light, the B value being a component of the excitation light, and the R value being a component of the fluorescence.

For example, in the white balance adjustment processing, among the R, G, and B pixel values included in the PDD image, the G value may be removed by appropriately adjusting a gain by which each of the R, G, and B pixel values is to be multiplied. Further, for example, in the demosaic processing, when each of the R value, the G value, and the B value is given to each pixel by interpolation, among the R, G, and B pixel values included in the PDD image, the G value may be removed. In addition, for example, in the color correction matrix processing, among the R, G, and B pixel values included in the PDD image, the G value may be removed by appropriately adjusting a color correction matrix by which an input matrix having, as a matrix element, each of the R, G, and B pixel values included in the PDD image is to be multiplied.

That is, the image processor 921 corresponds to an adjustment processing execution unit according to the present disclosure.

The display controller 922 generates a video signal for displaying the PDD image subjected to the first and second image processing under the control of the control unit 93. Further, the display controller 922 outputs the video signal to the display device 7 via the second transmission cable 8.

The wave detection processor 923 performs wave detection processing based on the PDD image subjected to only the first image processing among the first and second image processing.

Specifically, the wave detection processor 923 performs, based on pixel information (for example, luminance signal (Y signal)) of each pixel of a wave detection region which is at least a part of an entire image region of a PDD image of one frame, detection of contrast or a frequency component of an image in the wave detection region, detection of an average luminance value or maximum and minimum pixels in the wave detection region by a filter or the like, comparison with a threshold value, and detection of a histogram or the like (wave detection processing). Further, the wave detection processor 923 outputs, to the control unit 93, wave detection information (contrast, the frequency component, the average luminance value, the maximum and minimum pixels, the histogram, and the like) obtained through the wave detection processing. The control unit 93 is implemented by, for example, a CPU, an FPGA, or the like, and outputs a control signal via the first to third transmission cables 6, 8, and 10, thereby controlling operations of the light source device 3, the camera head 5, and the display device 7 and controlling the overall operation of the control device 9. As illustrated in FIG. 3, the control unit 93 includes a light source controller 931, an imaging controller 932, an evaluation value calculation unit 933, a focal position controller 934, and a brightness controller 935. Here, the focal position controller 934 and the brightness controller 935 correspond to an operation controller according to the present disclosure. Note that the functions of the light source controller 931, the imaging controller 932, the evaluation value calculation unit 933, the focal position controller 934, and the brightness controller 935 will be described in "Operation of Control Device" as described later.

The input unit 94 is implemented by an operation device such as a mouse, a keyboard, or a touch panel, and accepts a user operation by a user such as a doctor. Further, the input unit 94 outputs, to the control unit 93, an operation signal corresponding to the user operation.

The output unit 95 is implemented by a speaker, a printer, or the like, and outputs various information.

The storage unit 96 stores a program executed by the control unit 93, information necessary for processing performed by the control unit 93, and the like.

Operation of Control Device

Next, the operation of the control device 9 described above will be described.

Figure 5:
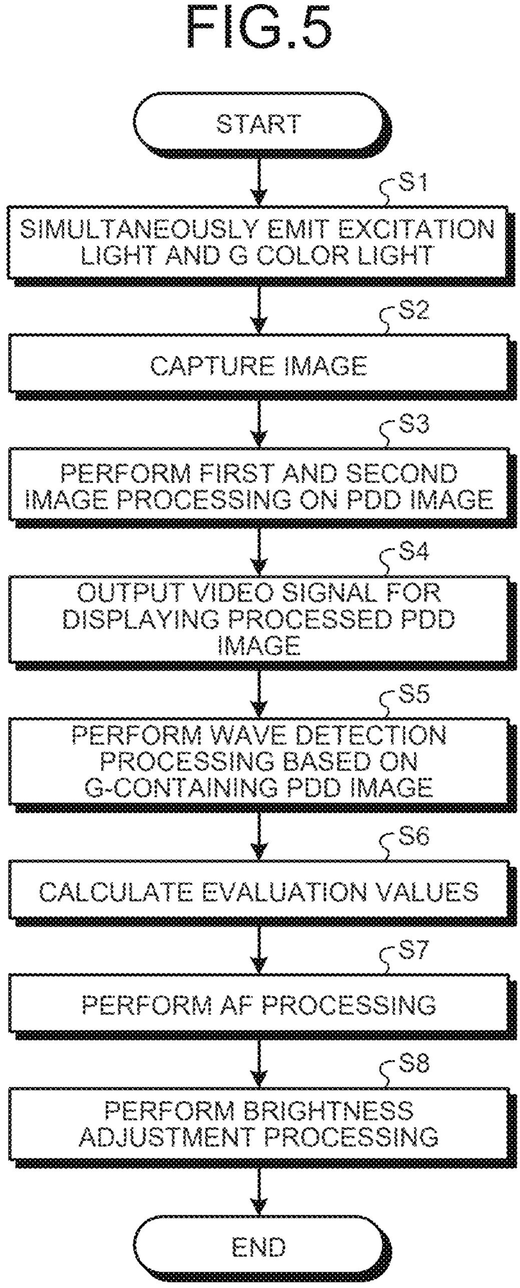
FIG. 5 is a flowchart illustrating an operation of the control device.
Figure 6:
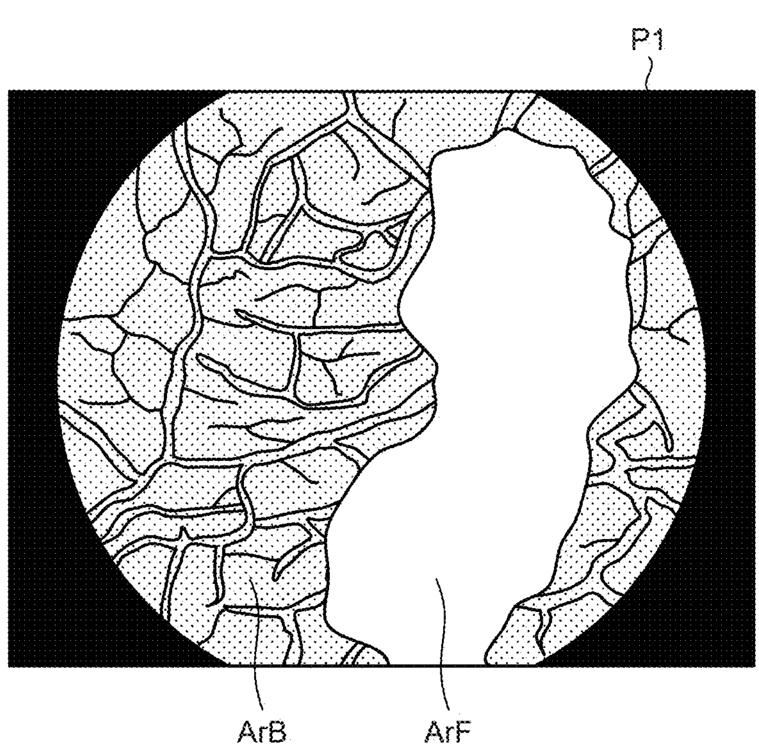
FIG. 6 is a diagram for describing an operation of the control device.

FIG. 5 is a flowchart illustrating the operation of the control device 9. FIG. 6 is a diagram for describing the operation of the control device 9. Specifically, FIG. 6 is a diagram illustrating a PDD image P1 of one frame. Note that, in FIG. 6, a fluorescent region ArF represented by white corresponds to a lesion in which protoporphyrin is excessively accumulated. Further, in FIG. 6, a background region ArB other than the fluorescent region ArF is represented by dots.

First, the light source controller 931 simultaneously drives the green LED 32 and the blue LED 33 (Step S1). That is, in Step S1, the light source controller 931 controls the light source device 3 to simultaneously emit the excitation light and the G color light.

After Step S1, the imaging controller 932 causes the image sensor 542 to capture subject images (excitation light, G color light, and fluorescence) at a predetermined frame rate (Step S2). Then, the imaging unit 54 sequentially generates PDD images P1 by capturing the subject images.

After Step S2, the image processor 921 sequentially performs the first and second image processing on the PDD image P1 (Step S3).

Here, in the PDD image P1 generated by the imaging unit 54, the fluorescent region ArF mainly contains a component of the fluorescence (a component of light in the red wavelength band). Here, in the PDD image P1 generated by the imaging unit 54, the background region ArB mainly contains a component of the excitation light (a component of light in the blue wavelength band) and a component of the G color light. On the other hand, in a general PDD image, the background region ArB mainly contains a component of the excitation light (a component of light in the blue wavelength band). That is, the color of the background region ArB is different between the PDD image P1 generated by the imaging unit 54 and the general PDD image. Therefore, in the first embodiment, the component of the G color light contained in the PDD image P1 is removed by performing the second image processing (adjustment processing) on the PDD image P1. As a result, the background region ArB of the PDD image P1 mainly contains the component of the excitation light (the component of the light in the blue wavelength band), and has substantially the same color as the background region ArB of the general PDD image.

Note that, in the following description, for convenience of explanation, the PDD image P1 from which the component of the G color light is removed by performing the second image processing (adjustment processing) in addition to the first image processing will be referred to as a processed PDD image. Further, the PDD image P1 subjected to only the first image processing among the first and second image processing is an image containing the component of the G color light, because the second image processing (adjustment processing) is not performed. In the following description, for convenience of explanation, the "PDD image P1 subjected to only the first image processing" will be referred to as a G-containing PDD image in order to distinguish it from the processed PDD image.

After Step S3, the display controller 922 sequentially generates video signals for displaying the processed PDD images, and sequentially outputs the video signals to the display device 7 (Step S4). As a result, the processed PDD images are sequentially displayed on the display device 7.

After Step S4, the wave detection processor 923 performs the wave detection processing based on pixel information of each pixel of a specific wave detection region in an entire image region of the G-containing PDD image (Step S5). Examples of the wave detection region may include a region including the image center of the G-containing PDD image. Then, the wave detection processor 923 outputs wave detection information obtained by the wave detection processing to the control unit 93.

After Step S5, the evaluation value calculation unit 933 calculates evaluation values (a focusing evaluation value, and first and second brightness evaluation values) based on the wave detection information obtained by the wave detection processing in Step S5 (Step S6).

Specifically, in Step S6, the evaluation value calculation unit 933 calculates, based on the wave detection information (the contrast or frequency component), the focusing evaluation value for evaluating a focusing state of an image in the wave detection region in the entire image region of the G-containing PDD image. For example, the evaluation value calculation unit 933 uses, as the focusing evaluation value, contrast obtained by the wave detection processing in Step S5 or the sum of high frequency components among frequency components obtained by the wave detection processing in Step S5. Note that the larger the focusing evaluation value, the more accurate the focusing is.

Further, in Step S6, the evaluation value calculation unit 933 calculates, based on the wave detection information (average luminance value), a first brightness evaluation value for changing a brightness of the image in the wave detection region in the entire image region of the G-containing PDD image to a reference brightness (changing the wave detection information (average luminance value) to a reference average luminance value). Here, there is a correlation between the G-containing PDD image and the processed PDD image because the G-containing PDD image and the processed PDD image are different only in regard to whether or not the component of the G color light is contained. Then, the evaluation value calculation unit 933 uses the correlation to calculate, based on the above-described first brightness evaluation value, a second brightness evaluation value for changing a brightness of the processed PDD image to a reference brightness.

Here, examples of the second brightness evaluation value may include an exposure time of each pixel in the image sensor 542, an analog gain multiplied in the signal processor 544, a digital gain multiplied in the first image processing (digital gain processing) performed by the image processor 921, and an amount of the excitation light supplied by the blue LED 33.

As described above, the light source controller 931 controls the operation of the light source device 3 so that the component of the G color light is contained in the captured image (G-containing PDD image) used for the calculation of the evaluation value (Step S6).

After Step S6, the focal position controller 934 performs AF processing for adjusting the focal position of the lens unit 51 (Step S7). The AF processing corresponds to a first control according to the present disclosure.

Specifically, in Step S7, the focal position controller 934 refers to the focusing evaluation value calculated in Step S6 and a current focal position detected by the focal position detecting unit 53. Then, the focal position controller 934 controls the operation of the lens driving unit 52 by a hill climbing method or the like while referring to the focusing evaluation value and the current focal position, thereby positioning the focus lens 511 at a focal position where the image in the wave detection region in the entire image region of the G-containing PDD image is focused. As a result, an image in a wave detection region in an entire image area of the processed PDD image is also focused.

After Step S7, the brightness controller 935 performs brightness adjustment processing for adjusting the brightness of the processed PDD image (Step S8). The brightness adjustment processing corresponds to a second control according to the present disclosure.

Specifically, in a case where the second brightness evaluation value calculated in Step S6 is the "exposure time", the brightness controller 935 outputs a control signal to the imaging unit 54 and uses an exposure time of each pixel of the image sensor 542 as the second brightness evaluation value. Further, in a case where the second brightness evaluation value calculated in Step S6 is the "analog gain", the brightness controller 935 outputs a control signal to the imaging unit 54 and uses an analog gain multiplied in the signal processor 544 as the second brightness evaluation value. Further, in a case where the second brightness evaluation value calculated in Step S6 is the "digital gain", the brightness controller 935 outputs a control signal to the observation image generation unit 92, and uses a digital gain multiplied in the first image processing (digital gain processing) performed by the image processor 921 as the second brightness evaluation value. Further, in a case where the second brightness evaluation value calculated in Step S6 is the "amount of the excitation light", the brightness controller 935 outputs a control signal to the light source device 3 and uses the amount of the excitation light supplied by the blue LED 33 as the second brightness evaluation value.

Steps S5 to S8 described above are repeatedly performed in a specific cycle. That is, the "AF processing" according to the first embodiment is continuous AF that is repeatedly performed in a specific cycle. In other words, the evaluation value calculation unit 933 sequentially calculates the evaluation values used for the first control in a specific cycle.

According to the first embodiment described above, the following effects are obtained.

The control device 9 according to the first embodiment controls the operation of the light source device 3 so that the component of the G color light is contained in the captured image (G-containing PDD image) used for the calculation of the evaluation values (Step S6).

Here, in the color filter 543, the G filter group 543*g*, which mainly transmits light in the green wavelength band, has more pixels than the R filter group 543*r* and the B filter group 543*b*, which mainly transmit light in the red and blue wavelength bands. In addition, light in the green wavelength band is light that contributes to brightness that is easy for humans to see. That is, the G-containing PDD image is an image having brightness that is sufficient and is easy for humans to see, as compared with the PDD image that does not contain the component of the G color light.

Therefore, with the control device 9 according to the first embodiment, the evaluation value may be appropriately calculated by performing the calculation of the evaluation value based on the G-containing PDD image, and the first and second controls may be performed appropriately by using the appropriate evaluation value. That is, an image suitable for observation may be generated.

By the way, the background region ArB of the PDD image P1 generated by the imaging unit 54 mainly contains the component of the excitation light and the component of the G color light. On the other hand, the background region ArB of the general PDD image mainly includes the component of the excitation light. That is, the color of the background region ArB is different between the PDD image P1 and the general PDD image.

Therefore, in the control device 9 according to the first embodiment, the adjustment processing for removing the component of the G color light contained in the PDD image P1 is performed. Therefore, the processed PDD image displayed on the display device 7 has the same color as the general PDD image. That is, it does not give a sense of incompatibility to users such as doctors.

Further, the light in the second wavelength band according to the present disclosure is the G color light in a narrow band that does not include the wavelength band of the fluorescence. That is, it is possible to generate an image that is suitable for observation without the change of color of the fluorescent region ArF (lesion) due to the G color light and that is not difficult to see the lesion.

Second Embodiment

Next, a second embodiment will be described.

In the following description, the same components as those in the first embodiment will be designated by the same reference numerals, and a detailed description thereof will be omitted or simplified.

Figure 7:
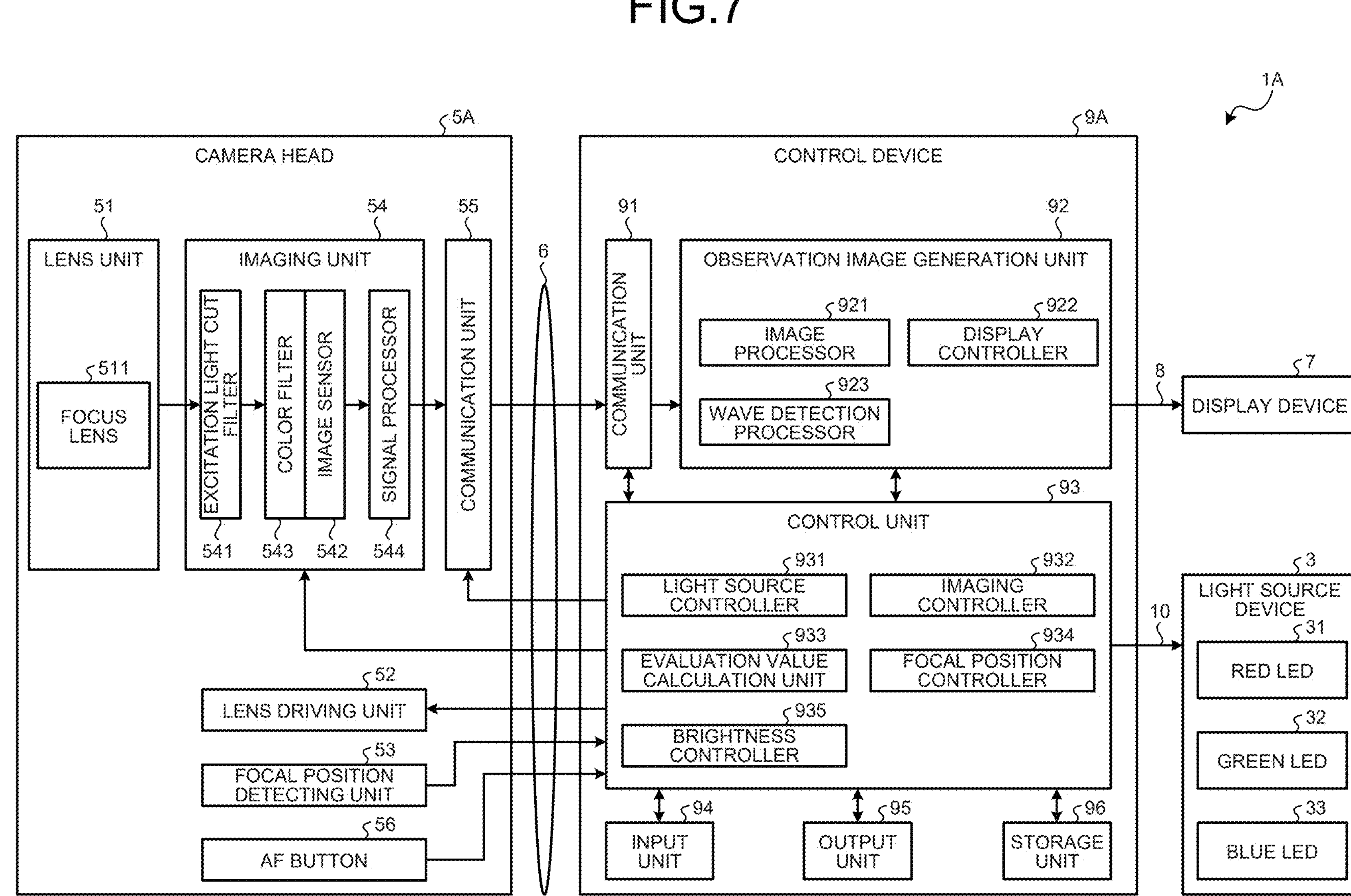
FIG. 7 is a block diagram illustrating a configuration of a medical observation system (a camera head and a control device) according to a second embodiment.

FIG. 7 is a diagram corresponding to FIG. 3, and is a block diagram illustrating a configuration of a medical observation system 1A (a camera head 5A and a control device 9A) according to the second embodiment.

The control device 9 according to the first embodiment described above performs continuous AF as the "AF processing".

On the other hand, the control device 9A according to the second embodiment performs AF processing according to a user operation (pressing) on an AF button 56 (FIG. 7) that is provided in the camera head 5A and receives the user operation for requesting execution of the AF processing. That is, the control device 9A performs one-touch AF as the "AF processing". The AF button 56 corresponds to an operation input unit according to the present disclosure.

Note that the camera head 5A according to the second embodiment has the same configuration as the camera head 5 described in the first embodiment, except that the AF button 56 is provided. Further, the control device 9A according to the second embodiment has the same configuration as the control device 9 described in the first embodiment described above, but a function executed by a control unit 93 is different.

Hereinafter, the functions executed by the control unit 93 will be described.

Figure 8:
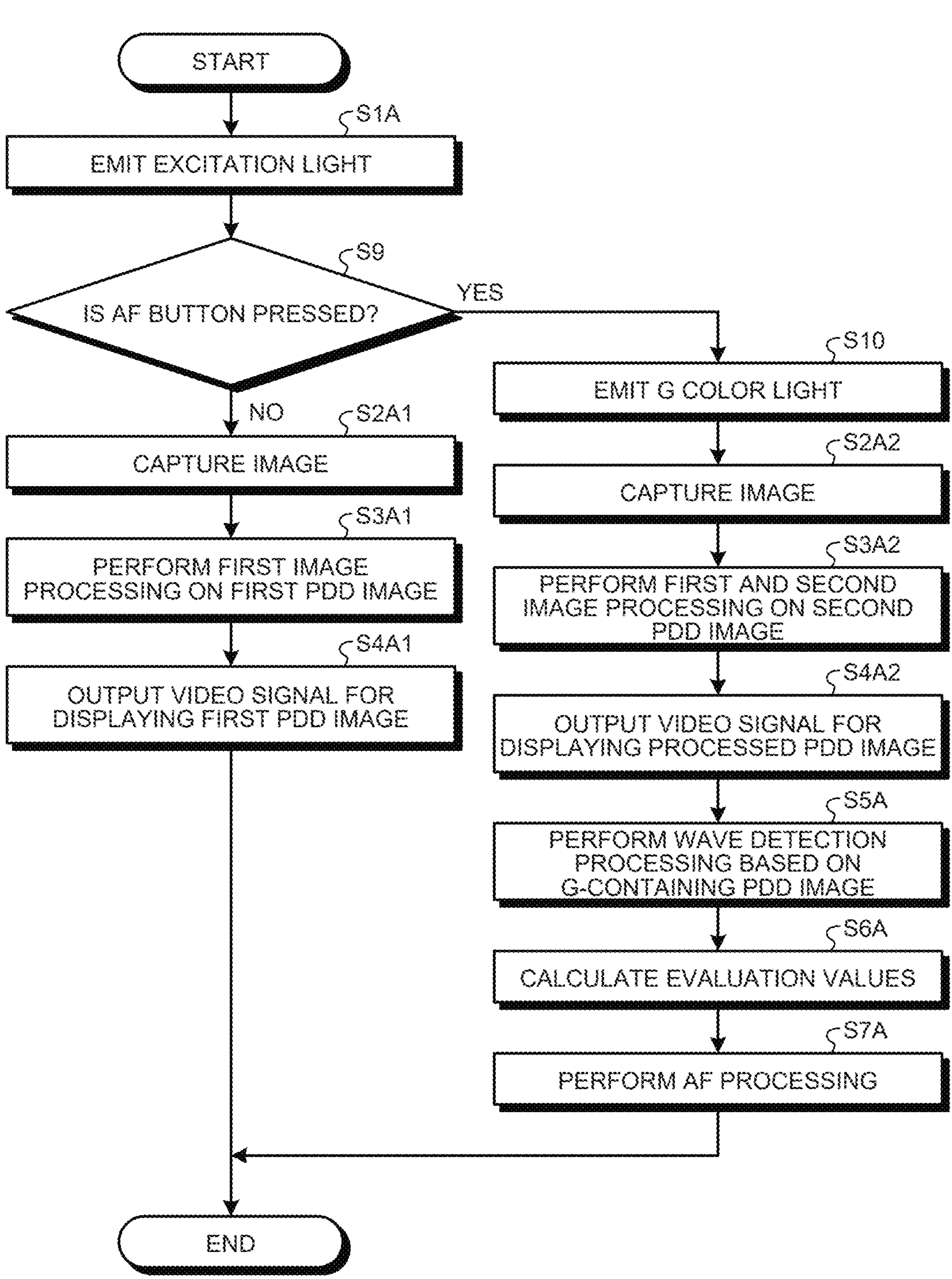
FIG. 8 is a flowchart illustrating an operation of the control device.

FIG. 8 is a flowchart illustrating an operation of the control device 9A.

First, a light source controller 931 drives a blue LED 33 (Step S1A). That is, the light source controller 931 controls a light source device 3 to emit only excitation light in Step S1A. Therefore, only the excitation light is radiated into the living body from a distal end of an insertion unit 2. Further, the excitation light radiated into the living body and reflected in the living body, and fluorescence that is emitted from protoporphyrin as the protoporphyrin accumulated in a lesion in the living body is excited are collected by an optical system in the insertion unit 2. Note that, in the following description, the excitation light and the fluorescence collected by the optical system in the insertion unit 2 are referred to as first subject images for convenience of explanation.

After Step S1A, the control unit 93 determines whether or not the AF button 56 is pressed (Step S9).

In a case where it is determined that the AF button 56 is not pressed (Step S9: No), an imaging controller 932 controls an image sensor 542 to capture the first subject images (excitation light and fluorescence) at a predetermined frame rate (Step S2A1). Then, an imaging unit 54 sequentially generates captured images by capturing the first subject images. In the following description, for convenience of explanation, the captured image generated by capturing the first subject images (excitation light and fluorescence) with the imaging unit 54 will be referred to as a first PDD image. The first PDD image is a general PDD image in which a background region mainly contains a component of the excitation light, because G color light is not emitted in Step S1A and a component of the G color light is not contained.

After Step S2A1, an image processor 921 sequentially performs first image processing on the first PDD image (Step S3A1).

After Step S3A1, a display controller 922 sequentially generates video signals for displaying the first PDD image subjected to the first image processing, and sequentially outputs the video signals to a display device 7 (Step S4A1). As a result, the first PDD image subjected to the first image processing is sequentially displayed on the display device 7.

On the other hand, in a case where it is determined that the AF button 56 is pressed (Step S9: Yes), the light source controller 931 drives a green LED 32 (Step S10). That is, in Step S10, the light source controller 931 controls the light source device 3 to emit the G color light, in addition to the excitation light in Step S10. Therefore, the excitation light and the G color light are radiated into the living body from the distal end of the insertion unit 2. Then, the excitation light radiated into the living body and reflected in the living body, the G color light reflected in the living body, and the fluorescence that is emitted from protoporphyrin as the protoporphyrin accumulated in a lesion in the living body is excited are collected by the optical system in the insertion unit 2. Note that, in the following description, the excitation light, the G color light, and the fluorescence collected by the optical system in the insertion unit 2 are referred to as second subject images for convenience of explanation. The second subject images are the same as the subject images described in the first embodiment described above.

After Step S10, the imaging controller 932 causes the image sensor 542 to capture the second subject images (excitation light, G color light, and fluorescence) at a predetermined frame rate (Step S2A2). Then, an imaging unit 54 sequentially generates captured images by capturing the second subject images. In the following description, for convenience of explanation, the captured image generated by capturing the second subject images (excitation light, G color light, and fluorescence) with the imaging unit 54 will be referred to as a second PDD image.

After Step S2A2, the image processor 921 sequentially performs the first image processing and second image processing on the second PDD image (Step S3A2).

The second PDD image subjected to the first and second image processing corresponds to the processed PDD image described in the first embodiment described above. Further, the second PDD image subjected to only the first image processing among the first and second image processing corresponds to the G-containing PDD image described in the first embodiment described above.

After Step S3A2, the control unit 93 performs Steps S4A2, S5A, S6A, and S7A similar to Steps S4 to S7 described in the first embodiment described above.

That is, Steps S5A, S6A, and S7A are performed only when the AF button 56 is pressed. Therefore, the "AF processing" according to the second embodiment is one-touch AF. In other words, an evaluation value calculation unit 933 calculates an evaluation value used for a first control in response to the user operation on the AF button 56.

As described above, also in the second embodiment, the light source controller 931 controls the operation of the light source device 3 so that the component of the G color light is contained in the captured image (G-containing PDD image) used for the calculation of the evaluation value (Step S6A), similarly to the first embodiment described above.

According to the second embodiment described above, in addition to the same effect as that of the first embodiment described above, the following effects are obtained.

A background region ArB of the second PDD image generated by the imaging unit 54 mainly contains the component of the excitation light and the component of the G color light. On the other hand, a background region ArB of the first PDD image generated by the imaging unit 54 mainly contains the component of the excitation light, similarly to the general PDD image. That is, the color of the background region ArB is different between the first PDD image and the second PDD image.

Therefore, in the control device 9A according to the second embodiment, adjustment processing for removing the component of the G color light contained in the second PDD image is performed. Therefore, the color of the PDD image displayed on the display device 7 does not change depending on whether the AF processing is performed by the one-touch AF or not, and thus it does not give a sense of incompatibility to users such as doctors.

Third Embodiment

Next, a third embodiment will be described.

In the following description, the same components as those in the first embodiment will be designated by the same reference numerals, and a detailed description thereof will be omitted or simplified.

In the first embodiment described above, the present disclosure is applied to the medical observation system 1 using a rigid endoscope (insertion unit 2).

Figure 9:
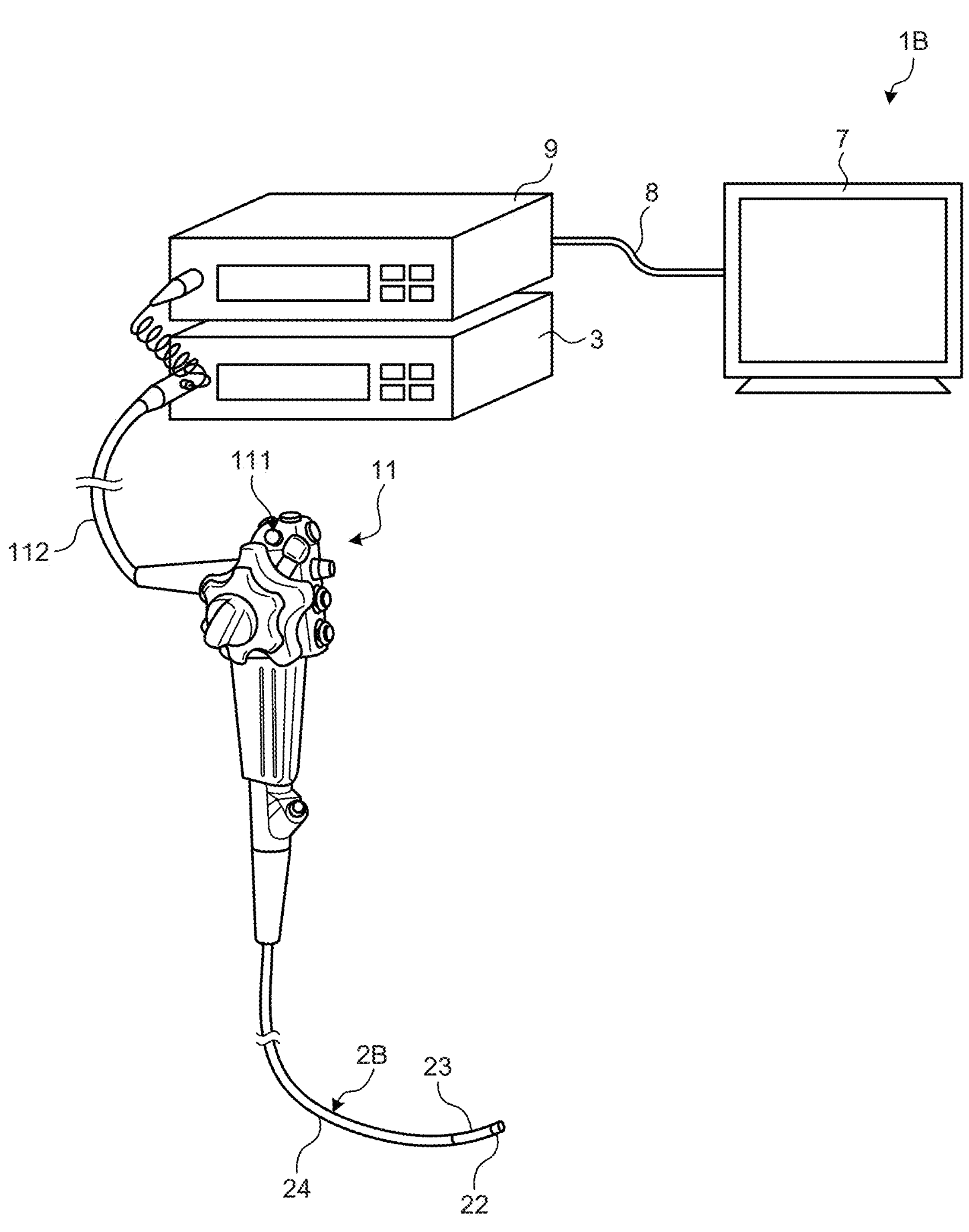
FIG. 9 is a diagram illustrating a configuration of a medical observation system according to a third embodiment.

On the other hand, in the third embodiment, the present disclosure is applied to a medical observation system using a so-called videoscope including an imaging unit provided on a distal end side of an insertion unit. FIG. 9 is a diagram illustrating a configuration of a medical observation system 1B according to the third embodiment.

As illustrated in FIG. 9, the medical observation system 1B according to the third embodiment includes an endoscope 11 that captures an in-vivo image of an observed region through insertion of an insertion unit 2B into a living body and outputs an image signal, a light source device 3 that generates illumination light emitted from a distal end of the endoscope 11, a control device 9 that processes an image signal output from the endoscope 11, and a display device 7 that is connected to the control device 9 via the second transmission cable 8 and displays an image based on the image signal processed in the control device 9.

As illustrated in FIG. 9, the endoscope 11 includes the insertion unit 2B that is flexible and has an elongated shape, an operating unit 111 that is connected to a proximal end of the insertion unit 2B and receives various operations, and a universal cord 112 that extends from the operating unit 111 in a direction different from a direction in which the insertion unit 2B extends and incorporates various cables connected to the light source device 3 and the control device 9.

As illustrated in FIG. 9, the insertion unit 2B includes a distal end unit 22, a bendable unit 23 that is bendable, is connected to a proximal end of the distal end unit 22, and includes a plurality of bending pieces, and a flexible tube unit 24 that is connected to a proximal end of the bendable unit 23, is flexible, and has an elongated shape.

Further, although not illustrated in detail, a component substantially similar to the imaging unit 54 described in the first embodiment described above is embedded in the distal end unit 22. Further, although not illustrated in detail, a component substantially similar to the communication unit 55 described in the first embodiment described above is embedded in the operating unit 111. Further, an image signal captured by the distal end unit 22 (imaging unit) is output to the control device 9 via the operating unit 111 and the universal cord 112.

Even in a case where a flexible endoscope (endoscope 11) is used as in the third embodiment described above, the same effect as that of the first embodiment described above is obtained.

Fourth Embodiment

Next, a fourth embodiment will be described.

In the following description, the same components as those in the first embodiment will be designated by the same reference numerals, and a detailed description thereof will be omitted or simplified.

In the first embodiment described above, the present disclosure is applied to the medical observation system 1 using a rigid endoscope (insertion unit 2).

On the other hand, in the fourth embodiment, the present disclosure is applied to a medical observation system using a surgical microscope that captures an enlarged image of a predetermined visual field region of the inside of a subject (the inside of the living body) or a surface of the subject (a surface of the living body).

Figure 10:
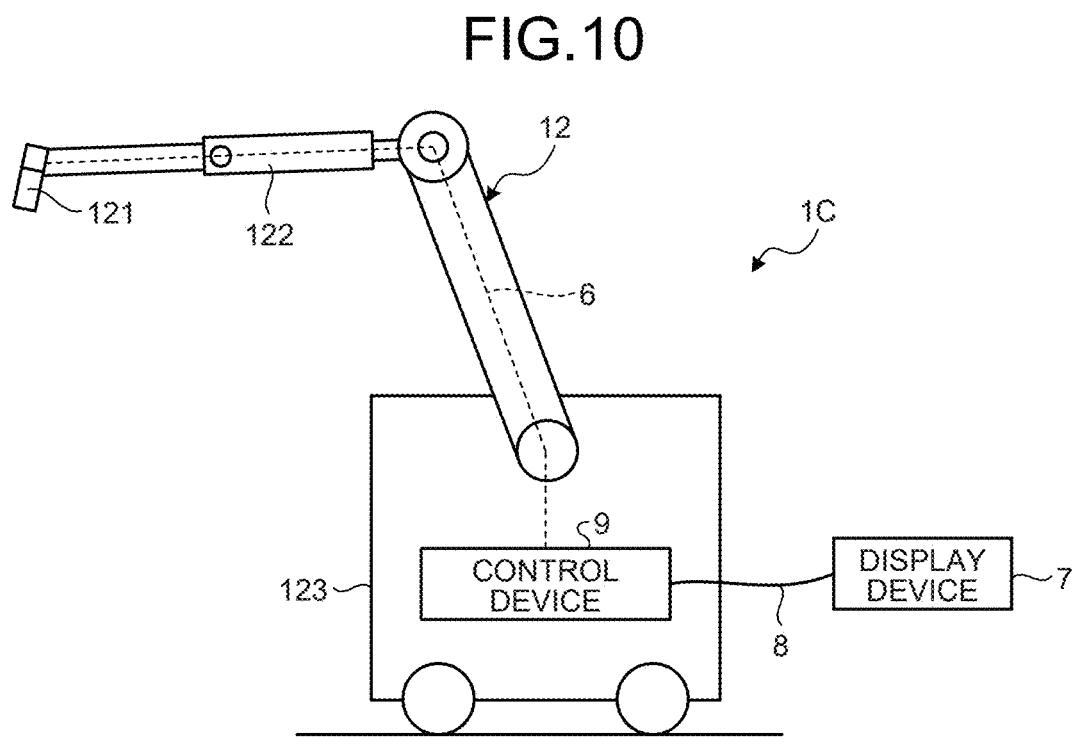

FIG. 10 is a diagram illustrating a configuration of a medical observation system 1C according to the fourth embodiment.

As illustrated in FIG. 10, the medical observation system 1C according to the fourth embodiment includes a surgical microscope 12 that captures an image for observing a subject and outputs an image signal, a control device 9 that processes the image signal output from the surgical microscope 12, and a display device 7 that is connected to the control device 9 via a second transmission cable 8 and displays an image based on the image signal processed in the control device 9.

As illustrated in FIG. 10, the surgical microscope 12 includes a microscope unit 121 that captures an enlarged image of a microfine region of the subject and outputs an image signal, a support unit 122 that includes an arm connected to a proximal end portion of the microscope unit 121 and rotatably supporting the microscope unit 121, and a base unit 123 that rotatably holds a proximal end portion of the support unit 122 and is movable on a floor.

Further, as illustrated in FIG. 10, the control device 9 is installed in the base unit 123. Further, although not illustrated in detail, the light source device 3 that generates illumination light radiated from the surgical microscope 12 to the subject is also installed in the base unit 123.

Note that the base unit 123 does not have to be movable on the floor, and may be fixed to a ceiling, a wall surface, or the like and support the support unit 122.

Although not illustrated in detail, components substantially similar to the imaging unit 54 and the communication unit 55 described in the first embodiment described above are embedded in the microscope unit 121. Further, the image signal captured by the microscope unit 121 (imaging unit) is output to the control device 9 via a first transmission cable 6 wired along the support unit 122.

Even in a case where the surgical microscope 12 is used as in the fourth embodiment described above, the same effect as that of the first embodiment described above is obtained.

Other Embodiments

Although the embodiments for carrying out the present disclosure have been described so far, the present disclosure should not be limited only to the above-described first to fourth embodiments.

In the above-described first, third, and fourth embodiments, the control device 9 calculates each of evaluation values used for the first and second controls based on the G-containing PDD image, but the present disclosure is not limited thereto. The medical control device according to the present disclosure may have, for example, a configuration in which only an evaluation value used for one of the first control or the second control based on the G-containing PDD image, as long as an evaluation value of at least one of the first control or the second control is calculated based on the G-containing PDD image.

In the above-described first to fourth embodiments, the light source device 3 may emit light in the blue wavelength band as excitation light in the first wavelength band, and may emit G color light as light in the second wavelength band. However, the present disclosure is not limited thereto, and other light may be adopted as the excitation light in the first wavelength band and the light in the second wavelength band, respectively. For example, the light in the second wavelength band according to the present disclosure is not limited to the G color light, and may also be white light, as long as the light is light in the green wavelength band. At this time, the first and second wavelength bands may partially overlap each other or do not have to overlap each other.

In the above-described first and second embodiments, a part of the camera head 5 or 5A and a part of the control device 9 or 9A may be provided in the connector CN1 or the connector CN2, for example.

Note that the following configurations also fall within the technical scope of the present disclosure.

Moreover, the below-described configurations may fall within a scope of the present disclosure.

(1) A medical control device including: a light source controller configured to control an operation of a light source configured to emit excitation light in a first wavelength band and light in a second wavelength band different from the first wavelength band; a captured image acquiring unit configured to acquire a captured image obtained by capturing an image of an observation target irradiated with light emitted from the light source; an evaluation value calculator configured to calculate, based on the captured image, an evaluation value used for at least one of a first control for controlling a focal position of an imaging device configured to generate the captured image or a second control for controlling a brightness of the captured image; an operation controller configured to perform, based on the evaluation value, at least one of the first control or the second control; and an adjustment processing execution unit configured to perform adjustment processing on the captured image, wherein the light source controller is configured to control the operation of the light source such that a component of the light in the second wavelength band is contained in the captured image used for the calculation of the evaluation value, and the adjustment processing execution unit is configured to perform the adjustment processing for removing the component of the light in the second wavelength band contained in the captured image.

(2) The medical control device according to (1), wherein the second wavelength band includes a green wavelength band.

(3) The medical control device according to (2), wherein the adjustment processing is white balance adjustment processing, and the component of the light in the second wavelength band is removed by multiplying, by a specific gain, a component of light in each of a red wavelength band, the green wavelength band, and a blue wavelength band contained in the captured image.

(4) The medical control device according to (2), wherein the adjustment processing is color correction matrix processing, and the component of the light in the second wavelength band is removed by multiplying a specific color correction matrix by an input matrix having, as a matrix element, a component of light in each of a red wavelength band, the green wavelength band, and a blue wavelength band contained in the captured image.

(5) The medical control device according to (2), wherein the adjustment processing is demosaic processing, and the component of the light in the second wavelength band is removed by removing a component of light in the green wavelength band when a component of light in each of a red wavelength band, the green wavelength band, and a blue wavelength band is given to each pixel included in the captured image.

(6) The medical control device according to any one of (1) to (5), wherein the light in the second wavelength band is light that does not include a wavelength band of fluorescence from the observation target excited by the excitation light.

(7) The medical control device according to any one of (1) to (6), wherein the evaluation value calculator is configured to sequentially calculate evaluation values used for the first control in a specific cycle.

(8) The medical control device according to any one of (1) to (6), wherein the evaluation value calculator is configured to calculate an evaluation value used for the first control in response to a user operation on an operation input unit, the user operation requesting execution of the first control.

(9) The medical control device according to any one of (1) to (8), wherein the excitation light is light in a blue wavelength band by which protoporphyrin is excited.

(10) A medical observation system including: a light source configured to emit excitation light in a first wavelength band and light in a second wavelength band different from the first wavelength band; an imaging device configured to generate a captured image by capturing an image of an observation target irradiated with light emitted from the light source; and the medical control device according to any one of (1) to (9), the medical control device controlling an operation of each of the light source and the imaging device.

According to the medical control device and the medical observation system, an image suitable for observation may be generated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising:

circuitry configured to:

determine whether an image sensor to capture an image is operating in a first mode in which a fluorescence image of an observation target is to be and a second mode in which parameters of the image to be captured are controlled;

in response to the image sensor being in the first mode, control an operation of a light source to emit excitation light in a first wavelength band, acquire a captured image of the observation target irradiated with light in the first wavelength band, wherein the observation target fluoresces in response to the excitation light to output light in a third wavelength band, and perform first image processing on the captured image of the observation target irradiated with the light in the first wavelength band which includes light in the third wavelength band;

in response to the image sensor being in the second mode, control the operation of the light source to simultaneously emit excitation light in the first wavelength band and light in a second wavelength band different from the first wavelength band;

acquire a captured image obtained by capturing an image of an observation target irradiated with light in the first wavelength band and in the second wavelength band emitted from the light source, wherein the observation target fluoresces in response to the excitation light to output light in a third wavelength band and reflects light in the second wavelength band to output light in the second wavelength band, the captured image including light components in the second and third wavelengths bands, the second and third wavelength bands being different;

perform the first image processing on the captured image of light in the second and third wavelength bands;

calculate, based on the captured image acquired while the observation target is irradiated with light in the first wavelength band and in the second wavelength band, an evaluation value used for at least one of a first control for controlling a focal position of the image sensor configured to generate the captured image or a second control for controlling a brightness of the captured image, wherein a component of the light in the second wavelength band is used for the calculation of the evaluation value; and perform, based on the evaluation value, at least one of the first control or the second control on the captured image of light in the second and third wavelength band subjected to the first image processing.

2. The medical control device according to claim 1, wherein the circuitry is configured to remove the component of light in the second wavelength band by demosaic processing, and when a component of light in each of a red wavelength band, a green wavelength band, and a blue wavelength band is given to each pixel included in the captured image, the component of light in the second wavelength band is deleted by deleting a light component in any of the red, green, and blue wavelength bands.

3. The medical control device according to claim 1, wherein the light in the second wavelength band does not include the third wavelength band.

4. The medical control device according to claim 1, wherein the circuitry is configured to sequentially calculate evaluation values used for the first control in a specific cycle in the second mode.

5. The medical control device according to claim 1, wherein the circuitry is configured to calculate the evaluation value used for the first control in response to a user operation, the user operation requesting execution of the first control in the second mode.

6. The medical control device according to claim 1, wherein the excitation light is light in a blue wavelength band by which protoporphyrin is excited.

7. A medical observation system comprising:

the light source configured to emit excitation light in the first wavelength band and light in the second wavelength band different from the first wavelength band;

the image sensor configured to generate the captured image of the observation target; and the medical control device according to claim 1, the medical control device controlling an operation of each of the light source and the image sensor.

8. The medical control device according to claim 1, wherein the circuitry is configured to remove the component of the light in the second wavelength band contained in the captured image after the evaluation value is calculated in the second mode.

9. The medical control device according to claim 8, wherein the second wavelength band includes a green wavelength band.

10. The medical control device according to claim 8, wherein the circuitry is further configured to delete the component of light in the second wavelength band by white balance adjustment processing, and the component of the light in the second wavelength band is removed by multiplying, by a specific gain, a component of light in each of a red wavelength band, a green wavelength band, and a blue wavelength band contained in the captured image.

11. The medical control device according to claim 8, wherein the circuitry is further configured to delete the component of light in the second wavelength band by color correction matrix processing, and the component of the light in the second wavelength band is removed by multiplying a specific color correction matrix by an input matrix having, as a matrix element, a component of light in each of a red wavelength band, a green wavelength band, and a blue wavelength band contained in the captured image.

12. The medical control device according to claim 8, wherein the circuitry is configured to output the captured image with the component of the light in the second wavelength band removed as an image to be displayed.

13. The medical control device according to claim 1, wherein the second and third wavelength bands do not overlap.

14. The medical control device according to claim 13, wherein the first and second wavelength bands do not overlap.

15. A medical control method comprising:

determining whether an image sensor is operating in a first mode or a second mode;

in response to the image sensor being in the first mode, acquiring a captured image of an observation target based on excitation light in a first wavelength band;

in response to the image sensor being in the second mode, controlling an operation of a light source configured to simultaneously emit excitation light in the first wavelength band and light in a second wavelength band different from the first wavelength band;

acquiring a captured image obtained by capturing an image of the observation target irradiated with light in the first wavelength band and in the second wavelength band emitted from the light source, wherein the observation target fluoresces in response to the excitation light to output light in a third wavelength band and reflects light in the second wavelength band to output light in the second wavelength band, the captured image including light components in the second and third wavelengths bands, the second and third wavelength bands being different;

calculating, based on the captured image acquired while the observation target is irradiated with light in the first wavelength band and in the second wavelength band, an evaluation value used for at least one of a first control for controlling a focal position of the image sensor configured to generate the captured image or a second control for controlling a brightness of the captured image, wherein a component of the light in the second wavelength band is used for the calculation of the evaluation value;

after calculating the evaluation value, removing the component of the light in the second wavelength band contained in the captured image;

performing, based on the evaluation value, at least one of the first control or the second control; and outputting the captured image with the component of the light in the second wavelength band removed as an image to be displayed.

16. The medical control method according to claim 15, wherein, in response to the first control or the second control is to be performed, controlling the light source to simultaneously emit excitation light in the first wavelength band and image light in the second wavelength band.

17. A non-transitory computer readable storage device having computer readable instructions that when executed by a processor cause the processor to:

determine whether an image sensor to capture an image is operating in a first mode in which a fluorescent image of an observation target is to be captured at a predetermined frame rate and a second mode in which parameters of the image to be captured are controlled;

in response to the image sensor being in the first mode, control an operation of a light source to emit excitation light in a first wavelength band, acquire a captured image of an observation target irradiated with light in the first wavelength band, wherein the observation target fluoresces in response to the excitation light to output light in a third wavelength band, and perform first image processing on the captured image of the observation target irradiated with the light in the first wavelength band which light in the third wavelength band;

in response to the image sensor being in the second mode, control the operation of the light source to simultaneously emit excitation light in the first wavelength band and light in a second wavelength band different from the first wavelength band;

acquire a captured image obtained by capturing an image of an observation target irradiated with light in the first wavelength band and in the second wavelength band emitted from the light source, wherein the observation target fluoresces in response to the excitation light to output light in a third wavelength band and reflects light in the second wavelength band to output light in the second wavelength band, the captured image including light components in the second and third wavelengths bands, the second and third wavelength bands being different;

perform the first image processing on the captured image of light in the second and third wavelength bands;

calculate, based on the captured image acquired while the observation target is irradiated with light in the first wavelength band and in the second wavelength band, an evaluation value used for at least one of a first control for controlling a focal position of the image sensor configured to generate the captured image or a second control for controlling a brightness of the captured image, wherein a component of the light in the second wavelength band is used for the calculation of the evaluation value; and perform, based on the evaluation value, at least one of the first control or the second control on the captured image of light in the second and third wavelength band subjected to the first image processing.

18. The non-transitory computer readable storage device according to claim 17, wherein, after the evaluation value is calculated the processor is further caused to:

remove the component of the light in the second wavelength band contained in the captured image; and output the captured image with the component of the light in the second wavelength band removed as an image to be displayed.

19. The non-transitory computer readable storage device according to claim 17, wherein the processor is configured to calculate an evaluation value used for the first control in response to a user operation, the user operation requesting execution of the first control.

20. The non-transitory computer readable storage device according to claim 17, wherein the processor is configured to sequentially calculate evaluation values used for the first control in a specific cycle.

* * * * *